United States Patent
Xiao et al.

(10) Patent No.: US 11,660,320 B2
(45) Date of Patent: May 30, 2023

(54) USE OF FAECALIBACTERIUM PRAUSNITZII IN PREPARATION OF MEDICINE FOR TREATING PATHOLOGICAL VENTRICULAR REMODELING AND/OR HEART FAILURE FOLLOWING MYOCARDIAL INFARCTION

(71) Applicant: Shanghai University, Shanghai (CN)

(72) Inventors: Junjie Xiao, Shanghai (CN); Qiulian Zhou, Shanghai (CN); Xue Pan, Shanghai (CN); Danni Meng, Shanghai (CN)

(73) Assignee: Shanghai University, Shanghai (CN)

( * ) Notice: Subject to any disclaimer, the term of this patent is extended or adjusted under 35 U.S.C. 154(b) by 0 days.

(21) Appl. No.: 17/490,734

(22) Filed: Sep. 30, 2021

(65) Prior Publication Data
US 2022/0401498 A1 Dec. 22, 2022

(30) Foreign Application Priority Data
Jun. 21, 2021 (CN) .......................... 202110684626.9

(51) Int. Cl.
*A61K 35/74* (2015.01)
*A61P 9/10* (2006.01)
*A61K 47/10* (2017.01)
*C12R 1/145* (2006.01)

(52) U.S. Cl.
CPC .............. *A61K 35/74* (2013.01); *A61K 47/10* (2013.01); *A61P 9/10* (2018.01); *C12R 2001/145* (2021.05)

(58) Field of Classification Search
None
See application file for complete search history.

(56) References Cited

U.S. PATENT DOCUMENTS

2017/0304374 A1* 10/2017 Honig .................... A61K 35/74
2021/0145897 A1* 5/2021 Kawahara ................ A61P 3/04

OTHER PUBLICATIONS

Cui et al., "Metagenomic and metabolomic analyses unveil dysbiosis of gut microbiota in chronic heart failure patients", Scientific Reports, vol. 8(635), pp. 1-15. (Year: 2018).*
ATCC, Faecalibacterium prausnitzii 27768 Product Sheet; ATCC Website. https://www.atcc.org/api/pdf/product-sheet?id=27768 (Accessed: Sep. 2022), pp. 1-6.*

* cited by examiner

*Primary Examiner* — Michelle F. Paguio Frising
*Assistant Examiner* — Grant C Currens
(74) *Attorney, Agent, or Firm* — JWIP & Patent Services, LLC; Jacob G. Weintraub, Esq.

(57) ABSTRACT

The present disclosure belongs to the technical field of biomedicine, and provides use of *Faecalibacterium prausnitzii* in preparation of a medicine for treating pathological ventricular remodeling and/or heart failure following myocardial infarction. The *Faecalibacterium prausnitzii* can improve pathological ventricular remodeling and/or heart failure caused by myocardial infarction in experimental animals, resume the systolic function, reduce the cardiac fibrosis, and inhibit the pathological myocardial hypertrophy of mice with myocardial infarction. Furthermore, the inactivated *Faecalibacterium prausnitzii* has no such improvement effect.

11 Claims, 4 Drawing Sheets

USE OF FAECALIBACTERIUM PRAUSNITZII IN PREPARATION OF MEDICINE FOR TREATING PATHOLOGICAL VENTRICULAR REMODELING AND/OR HEART FAILURE FOLLOWING MYOCARDIAL INFARCTION

CROSS REFERENCE TO RELATED APPLICATION

This application claims the priority of Chinese Patent Application No. 202110684626.9, entitled "Use of *Faecalibacterium prausnitzii* in preparation of medicine for treating pathological ventricular remodeling and/or heart failure following myocardial infarction" filed with the China National Intellectual Property Administration on Jun. 21, 2021, the entire content of which is incorporated in this application by reference.

TECHNICAL FIELD

The present disclosure belongs to the technical field of biomedicine, and in particular relates to use of *Faecalibacterium prausnitzii* in preparation of medicine for improving pathological ventricular remodeling and/or heart failure following myocardial infarction.

BACKGROUND ART

The heart is an organ that promotes blood circulation in humans and vertebrates. It mainly functions as a power provider for blood flowing to all parts of the body. Myocardial infarction commonly seen in ischemic heart disease/coronary artery disease is a leading cause of death worldwide. It mainly occurs due to the rupture of atherosclerotic plaque leading to thrombosis in the coronary artery lumen. The thrombosis blocks the blood from flowing to the distal myocardium, resulting in dead myocardial cells, necrosis of tissues in the infarct area, and replacement of dead myocardial cells with scar tissues. Myocardial infarction changes the morphology and function of a ventricle, causes pathological ventricular remodeling such as reduction of cardiac muscle thickness, ventricular dilation, hypertrophy of cardiac muscle cells in the distal infarction region, and weakened cardiac functions, and may further develop into heart failure or even lead to death. The pathological ventricular remodeling following myocardial infarction is a complex process involving signal molecule transduction, transformation of extracellular matrix, neurohormonal regulation and many other processes. Although there are currently medicine that deals with this process, heart failure caused by ventricular remodeling following myocardial infarction still happens with a very high mortality rate. Thus, the key step in preventing heart failure is to maintain the systolic function of the heart and prevent adverse ventricular remodeling after myocardial infarction. Therefore, in addition to the commonly used clinical methods, new approaches are still needed to prevent and treat pathological ventricular remodeling following myocardial infarction.

There are a huge number of microbiota in mammalian intestines, including bacteria, archaea, viruses and single-celled eukaryotes, most of which live in the intestines and thus called intestinal floras. The intestinal floras co-existing with its mammalian host for a long time, forming a symbiotic relationship. Thus, they help form an intestinal surface barrier to inhibit the growth and reproduction of pathogenic bacteria, regulate the host's immune function, assist the host in digesting food to provide vitamins, fatty acids and other nutrients, and control the absorption of nutrients. They also produce biologically active signal molecules through metabolism to keep the host healthy or cause diseases. The intestinal floras are affected by diseases. In patients with inflammatory bowel disease, type I or type II diabetes, atherosclerosis, hypertension, or heart failure, the diversity of intestinal flora is lower than that in healthy individuals, or the composition of the floras is changed. Hence, the diversity and composition of the intestinal floras is very important for the health of mammalian hosts.

*Faecalibacterium prausnitzii*, a species of Rumnencoccus, belongs to *Clostridium* under Firmicutes. It is commonly found in the intestines of mammals and is extremely sensitive to oxygen. It is one of the symbiotic anaerobes in the human body with the highest abundance among the floras in adult intestines, accounting for about 5% of the total floras. Its main fermentation product butyrate is a main energy source for colonic epithelial cells. Moreover, *Faecalibacterium prausnitzii* also regulates gene expression in its host, fights against inflammation, and promotes intestinal health, showing the potential as a probiotic. In various intestinal or metabolic diseases, the abundance of *Faecalibacterium prausnitzii* in feces is greatly reduced, showing another potential as a biomarker.

At present, research on the function of *Faecalibacterium prausnitzii* has been mainly conducted to deal with intestinal or metabolic diseases. There is no research focusing on other uses yet.

SUMMARY

In view of this, an objective of the present disclosure is to provide use of *Faecalibacterium prausnitzii* in preparation of a medicine for treating pathological ventricular remodeling and/or heart failure following myocardial infarction. The *Faecalibacterium prausnitzii* can improve pathological ventricular remodeling and/or heart failure caused by myocardial infarction in experimental animals, resume the systolic function, reduce the cardiac fibrosis, and inhibit the pathological myocardial hypertrophy of the mice with myocardial infarction.

The present disclosure provides use of *Faecalibacterium prausnitzii* in preparation of a medicine for treating pathological ventricular remodeling and/or heart failure following myocardial infarction.

Preferably, the *Faecalibacterium prausnitzii* may be *Faecalibacterium prausnitzii* VPI C13-51 deposited in American type Culture Collection (ATCC) with the accession number of ATCC 27768.

Preferably, the *Faecalibacterium prausnitzii* may be obtained by culturing in a strictly anaerobic environment with a modified reinforced Clostridial culture medium.

Preferably, a dosage form of the medicine may be a liquid formulation or a solid formulation.

Preferably, when the dosage form of the medicine is a liquid formulation, a concentration of viable bacteria in the liquid formulation may be $10^9$-$10^{12}$ colony-forming units (CFU)/ml.

Preferably, the concentration of viable bacteria in the liquid formulation may be $10^{10}$-$10^{11}$ CFU/ml.

Preferably, the medicine may be obtained by suspending the *Faecalibacterium prausnitzii* in a phosphate buffer.

Preferably, the phosphate buffer may also include glycerol in a volume percentage of 10%.

Preferably, the medicine may be an oral formulation.

The present disclosure provides use of *Faecalibacterium prausnitzii* in preparation of a medicine for treating pathological ventricular remodeling and/or heart failure following myocardial infarction. The *Faecalibacterium prausnitzii* can improve pathological ventricular remodeling and/or heart failure caused by myocardial infarction in experimental animals, resume the systolic function, reduce the cardiac fibrosis, and inhibit the pathological myocardial hypertrophy of the mice with myocardial infarction.

In the present disclosure, the host's intestinal tract is supplemented with *Faecalibacterium prausnitzii* cultured in vitro as an exogenous strain. The strain functions in the intestinal tract and improves pathological ventricular remodeling and/or heart failure following myocardial infarction.

Further, the present disclosure uses *Faecalibacterium prausnitzii* in a liquid formulation by oral administration to individual mice after occurrence of myocardial infarction. The *Faecalibacterium prausnitzii* can improve the pathological ventricular remodeling following myocardial infarction and partially restore the cardiac functions. Thus, the objective of use of *Faecalibacterium prausnitzii* as a probiotic or a medicine to treat pathological remodeling following myocardial infarction is achieved.

Further, the present disclosure provides the use of *Faecalibacterium prausnitzii* in mice suffered from myocardial infarction, in which use the *Faecalibacterium prausnitzii* is cultured in vitro and supplemented back to the mice suffered from myocardial infarction with a suspension thereof. The results of mouse cardiac ultrasound show that supplementation of *Faecalibacterium prausnitzii* back to the mice with myocardial infarction enhances the heart systolic function, while supplementation of inactivated *Faecalibacterium prausnitzii* cannot restore the heart systolic function. In terms of the area of cardiac muscle cells, the degree of pathological hypertrophy of cardiac muscle cells in mice with myocardial infarction is lowered after supplementation of *Faecalibacterium prausnitzii* but not lowered after supplementation of inactivated *Faecalibacterium prausnitzii*. In terms of the fibrosis in the injured area, the degree of fibrosis is reduced by supplementation of *Faecalibacterium prausnitzii*, but not reduced by supplementation of inactivated *Faecalibacterium prausnitzii*. The *Faecalibacterium prausnitzii* supplemented in the present disclosure is a viable strain with biological activity. Its inactive or dead form does not improve the pathological ventricular remodeling following myocardial infarction.

DETAILED DESCRIPTION OF THE EMBODIMENTS

Figure 1:
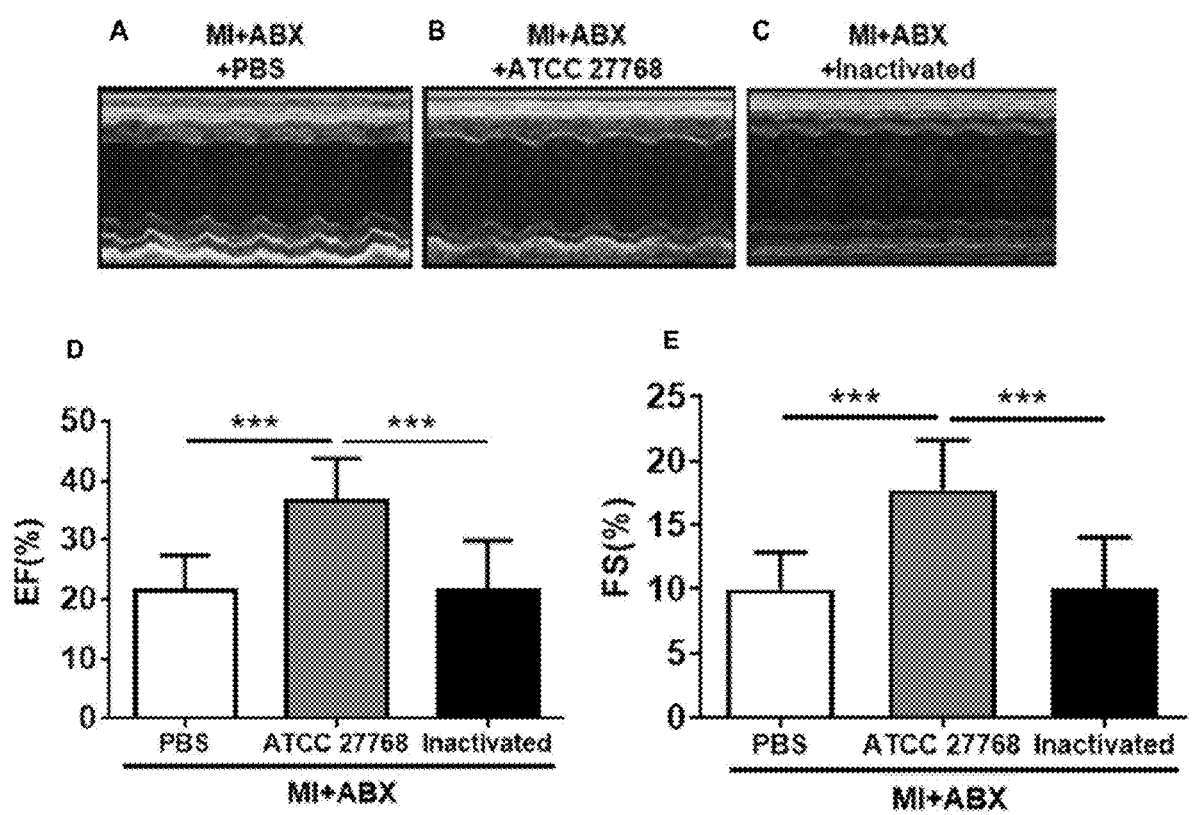
FIG. 1 shows the effect of supplementation of *Faecalibacterium prausnitzii* on heart systolic function of mice with myocardial infarction detected by echocardiography. Panel A represents the results of echocardiography after supplementation of phosphate-buffered saline (PBS) to mice with myocardial infarction. Panel B represents the results of echocardiography after supplementation of *Faecalibacterium prausnitzii* to mice with myocardial infarction. Panel C represents the results of echocardiography after supplementation of inactivated *Faecalibacterium prausnitzii* to mice with myocardial infarction. Panel D represents the statistical results of left ventricular ejection fraction after supplementation of PBS, *Faecalibacterium prausnitzii* or inactivated *Faecalibacterium prausnitzii* to mice with myocardial infarction, which shows that the supplementation of *Faecalibacterium prausnitzii* can increase the left ventricular ejection fraction of the mice with myocardial infarction, while the inactivation group does not have this effect. Panel E represents the statistical results of left ventricular fractional shortening after supplementation of PBS, *Faecalibacterium prausnitzii* or inactivated *Faecalibacterium prausnitzii* to mice with myocardial infarction, which shows that the supplementation of *Faecalibacterium prausnitzii* can increase the left ventricular fractional shortening of the mice with myocardial infarction, while the inactivation group does not have this effect.

The present disclosure provides use of *Faecalibacterium prausnitzii* in preparation of a medicine for treating pathological ventricular remodeling and/or heart failure following myocardial infarction.

In the present application, the *Faecalibacterium prausnitzii* may be *Faecalibacterium prausnitzii* VPI C13-51 deposited in American Type Culture Collection (ATCC) with the accession number of ATCC 27768. In a specific implementation process of the present disclosure, the *Faecalibacterium prausnitzii* VPI C13-51 may be preferably purchased from the ATCC.

In the present disclosure, the *Faecalibacterium prausnitzii* may be obtained by culturing in a strictly anaerobic environment with a modified reinforced Clostridial culture medium preferably purchased from Beijing Coolaber Technology Co., Ltd. (Coolaber, DZSL0529). The composition of the modified reinforced Clostridial culture medium is shown in Table 1.

TABLE 1

Composition of modified reinforced *Clostridial* culture medium

| Component | Concentration |
| --- | --- |
| Tryptose | 10.0 g/L |
| Beef extract | 10.0 g/L |
| Yeast extract | 3.0 g/L |
| Dextrose | 5.0 g/L |
| NaCl | 5.0 g/L |
| Soluble starch | 1.0 g/L |
| L-eysteine HCl | 0.5 g/L |
| Resazurin (0.025%) | 4 ml/L |
| Deionized (DI) water | 1,000 ml |
| Agar | 15 g/L (necessary for solid medium) |
| pH | 6.8 |

In the present disclosure, when preparation is completed, the modified reinforced Clostridial culture medium may be preferably divided into anaerobic containers for sterilization. The anaerobic containers may be preferably anaerobic culture tubes, and the sterilization may be preferably sterilization at a high temperature and a high pressure, preferably at 0.1 Mpa and 121° C. for 20 min. In the present disclosure, when the sterilization is completed, the modified reinforced Clostridial culture medium may be used to carry out inoculation of the *Faecalibacterium prausnitzii* for strictly anaerobic culture. The strictly anaerobic culture may be preferably suspension culture in a strictly anaerobic environment. In the present disclosure, the anaerobic culture may be preferably carried out in an anaerobic incubator (Thermo Scientific 1029 anaerobic incubator). After the incubator is externally connected to nitrogen and hydrogen, the gas in the incubator may be repeatedly replaced for 20 times to remove most of the oxygen therein. Then, a palladium catalyst and silica gel particles may be added to the incubator. The palladium catalyst can catalyze reaction of hydrogen with the remaining oxygen in the incubator, generating water which can then be absorbed by the silica gel, and thereby creating a strictly anaerobic environment in the incubator. In the anaerobic incubator, the dry powder of *Faecalibacterium prausnitzii* VPI C13-51 purchased from ATCC may be resuscitated according to the product instructions. In the anaerobic incubator, the resuscitated *Faecalibacterium prausnitzii* suspension may be taken by dipping a sterile inoculation loop in the suspension, and streaked on the modified reinforced Clostridial solid culture medium. After cultivation for 48 h, single colonies on the solid medium may be picked up for suspension culture. Specifically, in the anaerobic incubator, 35 ml of the modified reinforced Clostridial culture medium may be taken into a 50 ml sterile centrifuge tube, and the single colonies picked up may be placed therein and cultured for 48 h.

In the present disclosure, a dosage form of the medicine may be preferably a liquid formulation or a solid formulation. When the dosage form of the medicine is a liquid formulation, the concentration of viable bacteria in the liquid formulation may be $10^9$-$10^{12}$ CFU/ml, more preferably $10^9$-$10^{11}$ CFU/ml, and most preferably $5 \times 10^{10}$ CFU/ml. In the present disclosure, the medicine may be obtained by suspending the *Faecalibacterium prausnitzii* in a phosphate buffer. In the present disclosure, the phosphate buffer may be preferably 1×phosphate buffer at a pH of preferably 7.3 and preferably include glycerol in a volume percentage of 10%. In the present disclosure, the glycerol is used to protect the activity of the bacteria at a low temperature. In a specific implementation process of the present disclosure, after the *Faecalibacterium prausnitzii* is obtained with the modified reinforced Clostridial culture medium, solid-liquid separation may be carried out to collect the bacteria followed by resuspension of the bacteria in the phosphate buffer to reach a viable bacterium concentration within the above defined range. In the present disclosure, the solid-liquid separation may be carried out by preferably centrifugation at preferably 8,000-10,000 rpm, more preferably 8,500-9,500 rpm, most preferably 9,000 rpm for preferably 8-12 min, more preferably 10 min. In the present disclosure, after the centrifugation, the bacteria may be collected and resuspended in the phosphate buffer. In the present disclosure, the bacteria may be preferably washed with the phosphate buffer for 1-3 time(s), more preferably 2 times, centrifuged and collected again. The bacterial cells may then be resuspended in the phosphate buffer containing glycerol to reach a viable bacterium concentration within the above defined range to obtain a liquid formulation. The liquid formulation may be used directly or stored at a low temperature, preferably at −80° C.

In the present disclosure, the medicine may be preferably an oral formulation and administered orally. In the present disclosure, when the subject is a mouse, the medicine may have a concentration of preferably $10^8$-$10^9$ CFU/100 µl, more preferably $5 \times 10^8$ CFU/100 µl, and administered preferably by gavage at a dose of preferably 100-300 µl/mouse, more preferably 200 µl/mouse, with a frequency of preferably 3 times a week for 8 weeks. In the present disclosure, when the subject is a human being, the medicine may be orally administered at preferably $1 \times 10^7$ CFU/day.

The technical solutions provided by the present disclosure will be described in detail below with reference to embodiments, but the embodiments should not be construed as limiting the claimed scope of the present disclosure.

Example 1

Cultivation and preservation of *Faecalibacterium prausnitzii*

The *Faecalibacterium prausnitzii* VPI C13-51 was purchased from ATCC (ATCC 27768). A modified reinforced Clostridial culture medium (ATCC Medium: 2107 Modified Reinforced Clostridial) was used. Specifically, the culture medium was purchased from Beijing Coolaber Technology Co., Ltd. (Coolaber, DZSL0529). The composition of the modified reinforced Clostridial culture medium is shown in Table 1.

The culture medium as shown in Table 1 was divided into anaerobic tubes, sterilized at a high temperature and a high pressure (0.1 Mpa, 121° C., 20 min), and then subjected to suspension cultivation of *Faecalibacterium prausnitzii* in a strictly anaerobic environment.

Before the end of the cultivation, *Faecalibacterium prausnitzii* was cultured with the above plate culture medium for counting. 1.5 ml sterile EP tubes were used to dilute the original bacterial suspension in a concentration gradient with sterile PBS. The dilution factor was 10, 100, $1\times10^3$, $1\times10^4$, $1\times10^5$, $1\times10^6$, $1\times10^7$, and $1\times10^8$. Specifically, 100 μl of well-mixed bacterial suspension was added to a 1.5 ml EP tube containing 900 μl of sterile PBS with a micropipette, and mixed uniformly, thus making a 10-fold dilution. After the mixing, 100 μl of bacterial suspension was taken from the EP tube with the 10-fold dilution, added to an EP tube containing 900 μl of sterile PBS, and mixed uniformly, thus making a 100-fold dilution. Subsequent dilutions were carried out by taking 100 μl of bacterial solution from the EP tube with the previous dilution, and adding to a subsequent EP tube containing 900 μl of sterile PBS, and repeating the operations for sequential dilutions until a $1\times10^8$-fold diluted bacterial suspension was obtained.

100 μl of bacterial suspension was taken from the $1\times10^6$-, $1\times10^7$-, and $1\times10^8$-fold diluted bacterial suspensions respectively and dripped into a sterile solid plate, spread evenly with a glass spreading rod, sealed with a parafilm, and subjected to inverted culture in a strictly anaerobic environment. 3 plates were prepared for each dilution factor. When colonies grew, the plates that can be counted (the colonies were not dense and can be clearly distinguished) were counted. The number of colonies on 3 plates with the same dilution factor was averaged to obtain the number of colonies per 100 μl of the diluted suspension from the original bacterial suspension with that dilution factor, and expressed in CFU. Finally, the average number was multiplied by the dilution factor to obtain the number of colonies per 100 μl of the original bacterial suspension. In this experiment, the colonies on the plates with $1\times10^8$ dilution were uniformly distributed and clearly distinguishable, with counts of 214, 237, and 223 respectively and the average colony number of 228. The number of colonies in the original bacterial suspension was calculated to be $2.28\times10^{11}$ CFU/ml.

After cultivation, the bacteria-containing suspension was centrifuged at 9,000 rpm for 10 min based on the counting results. The bacteria were resuspended twice in sterile PBS, and finally resuspended in sterile PBS containing 10% of glycerol and stored at a concentration of $5\times10^{10}$ CFU/ml at −80° C.

Example 2

1. Establishment of a mouse (C57B/6) myocardial infarction model: a mouse model of myocardial infarction was established by ligating the left anterior descending coronary artery of a mouse heart. Specifically, a chloral hydrate solution having a mass percentage of 4% was used to anesthetize a mouse by intraperitoneal injection at a dose of 10 μl/g. A depilatory cream was used to remove the hair in the area from the ventral neck to the xiphoid. The skin in the middle of the neck was incised with micro scissors to expose the trachea, and a ventilator catheter was inserted into the trachea through an indwelling needle with a frequency set at 120 breaths/min. Afterwards, under a stereoscope (purchased from Motic Medical Diagnostic System Co., Ltd.), the left chest skin and muscles of the mouse were incised laterally with micro scissors and micro tweezers to make a small incision of about 0.8 cm. The muscles in the fourth intercostal space were bluntly separated with micro tweezers to expose the heart. Then the left anterior descending coronary artery was ligated with a 7-0 suture needle. Finally, the ribs, muscles and skin were sutured with a 5-0 suture thread and a suture needle. The surgical site was disinfected with iodophor. The anesthetized mouse after the surgery was placed on an electric blanket at a constant temperature of 37° C. When it regained its ability to move, it was raised in the original environment. 8 weeks later, the systolic function of mice with myocardial infarction was detected by a cardiac ultrasound imaging system for small animals. The decrease in left ventricular ejection fraction and left ventricular fractional shortening of mice with myocardial infarction indicated that the myocardial infarction model was successfully established.

2. Antibiotic (ABX) treatment of mice with myocardial infarction was carried out with the specific method as follows.

ABX was prepared according to the formula shown in Table 2.

TABLE 2

| Composition of antibiotics (ABX) | |
|---|---|
| Ampicillin (Sigma) | 0.25 mg/ml |
| Metronidazole (Sigma) | 0.25 mg/ml |
| Neomycin (Sigma) | 0.25 mg/ml |
| Vancomycin (Sigma) | 0.125 mg/ml |

The 4 antibiotic powders were taken in the dark, dissolved with sterilized double-distilled water in an ultra-clean workbench to prepare the ABX solution. The ABX solution was added into sterilized drinking water bottles for mice and protected from light by wrapping the bottles with aluminum foil paper. The ABX solution was prepared every 2 days to prevent water deterioration. The ABX solution was used to replace the daily drinking water for the mice for a total of 7 days. After the 7 days, the mice were given normal sterilized water.

3. Transplantation of *Faecalibacterium prausnitzii*

The experiment included 3 groups: sterile PBS group, *Faecalibacterium prausnitzii* (ATCC 27768) transplantation group, and inactivation group. The mice used in the 3 groups were all the above mice with myocardial infarction subjected to the above ABX treatment. Starting from the first day after completion of the ABX treatment, the mice were treated by gavage with a disposable 1 ml sterile syringe and 8 gauge curved gavage needle. The specific method was as follows.

In the first group, the PBS group, mice were administered with sterile PBS by gavage at a dose of 200 μl/mouse, 3 times a week for 8 weeks.

In the second group, the *Faecalibacterium prausnitzii* (ATCC 27768) transplantation group, the stored $5\times10^{10}$ CFU/ml bacterial suspension mentioned in Example 1 was diluted with sterile PBS to a concentration of $5\times10^{10}$ CFU/100 μl PBS, and given to the mice by gavage, 3 times a week for 8 weeks.

In the third group, the inactivation group, the *Faecalibacterium prausnitzii* bacterial suspension with a concentration of $5\times10^8$ CFU/100 μl PBS was sterilized at 0.1 Mpa and 121° C. for 20 min. After cooling, the mice in the inactivation group were administered by gavage 3 times a week for 8 weeks.

Figure 2:
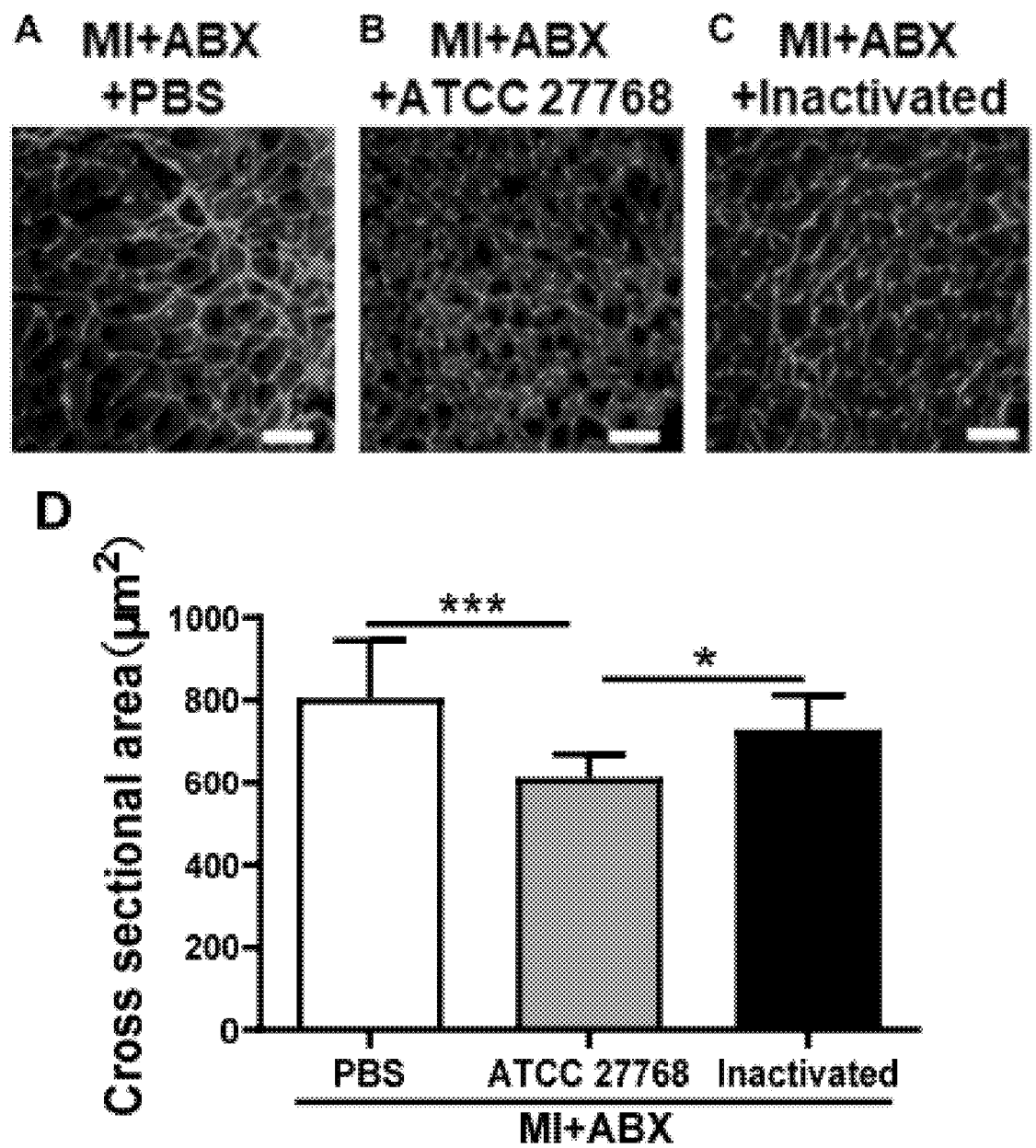
FIG. 2 shows the effect of supplementation of *Faecalibacterium prausnitzii* on cross-sectional areas of cardiac muscle fibers of mice with myocardial infarction detected by wheat germ agglutinin (WGA) staining. Panel A represents the results of WGA staining after supplementation of PBS to mice with myocardial infarction. Panel B represents the results of WGA staining after supplementation of *Faecalibacterium prausnitzii* to mice with myocardial infarction. Panel C represents the results of WGA staining after supplementation of inactivated *Faecalibacterium prausnitzii* to mice with myocardial infarction. Panel D represents the statistical results of cross-sectional areas of cardiac muscle fibers of mice with myocardial infarction after supplementation of PBS, *Faecalibacterium prausnitzii* or inactivated *Faecalibacterium prausnitzii* to mice with myocardial infarction, which shows that the supplementation of *Faecalibacterium prausnitzii* can reduce the cross-sectional areas of cardiac muscle fibers of the mice with myocardial infarction, while the inactivation group does not have this effect.
Figure 3:
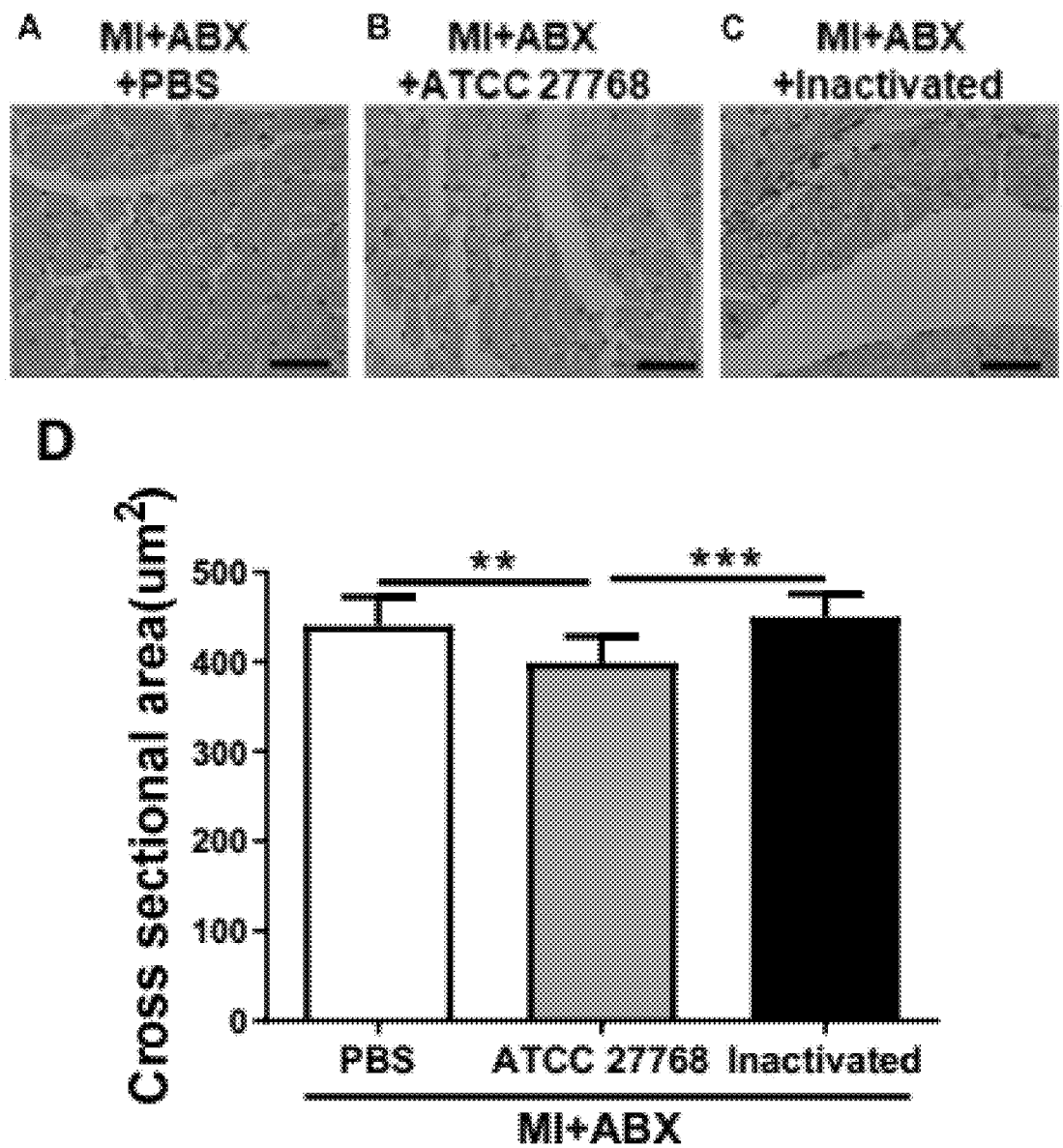
FIG. 3 shows the effect of supplementation of *Faecalibacterium prausnitzii* on cross-sectional areas of cardiac muscle fibers of mice with myocardial infarction detected by hematoxylin and eosin (HE) staining. Panel A represents the results of HE staining after supplementation of PBS to mice with myocardial infarction. Panel B represents the results of HE staining after supplementation of *Faecalibacterium prausnitzii* to mice with myocardial infarction. Panel C represents the results of HE staining after supplementation of inactivated *Faecalibacterium prausnitzii* to mice with myocardial infarction. Panel D represents the statistical results of cross-sectional areas of cardiac muscle fibers of mice with myocardial infarction after supplementation of PBS, *Faecalibacterium prausnitzii* or inactivated *Faecalibacterium prausnitzii* to mice with myocardial infarction, which shows that the supplementation of *Faecalibacterium prausnitzii* can reduce the cross-sectional areas of cardiac muscle fibers and pathological cardiac hypertrophy of the mice with myocardial infarction, while the inactivation group does not have this effect.
Figure 4:
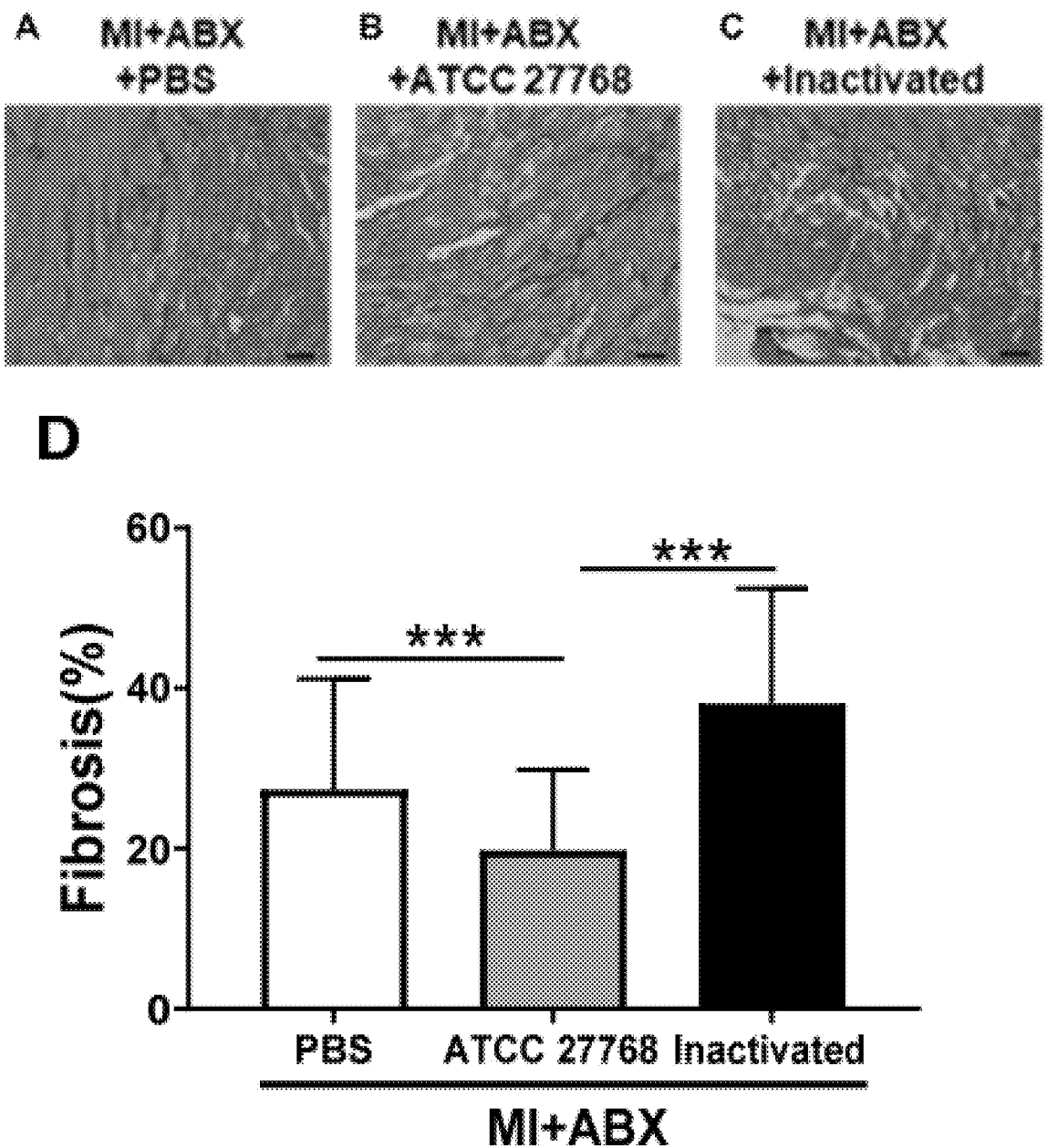
FIG. 4 shows the effect of supplementation of *Faecalibacterium prausnitzii* on degree of cardiac fibrosis of mice with myocardial infarction detected by Masson's trichrome staining. Panel A represents the results of Masson's trichrome staining after supplementation of PBS to mice with myocardial infarction. Panel B represents the results of Masson's trichrome staining after supplementation of *Faecalibacterium prausnitzii* to mice with myocardial infarction. Panel C represents the results of Masson's trichrome staining after supplementation of inactivated *Faecalibacterium prausnitzii* to mice with myocardial infarction. Panel D represents the statistical results of cardiac fibrosis of mice with myocardial infarction after supplementation of PBS, *Faecalibacterium prausnitzii* or inactivated *Faecalibacterium prausnitzii* to mice with myocardial infarction, which shows that the supplementation of *Faecalibacterium prausnitzii* can reduce cardiac fibrosis of the mice with myocardial infarction, while the inactivation group does not have this effect.

After the 8 weeks, the experiment was over. The systolic function of the heart was detected with a cardiac ultrasound imaging system for small animals (Vevo2100, Visual Sonics). Then the mice were euthanized and the hearts thereof were taken out through dissection. The heart samples were subjected to frozen tissue sectioning and WGA staining (FIG. 2) to detect the change of the cross-sectional area of cardiac muscle fibers. The staining results and statistical results showed that *Faecalibacterium prausnitzii* supplementation reduced the cross-sectional area of cardiac muscle fibers of mice with myocardial infarction while the inactivation group did not have the effect of reducing the area. The heart samples were embedded with paraffin, sectioned and subjected to HE staining (FIG. 3) to detect the change of the cross-sectional area of cardiac muscle fibers. The staining results and statistical results showed that *Faecalibacterium prausnitzii* supplementation reduced the cross-sectional area of cardiac muscle fibers of mice with myocardial infarction while the inactivation group did not have the effect of reducing the area. Masson's trichrome staining (FIG. 4) was carried out to detect the area of cardiac fibrous tissue. The staining results and statistical results showed that the *Faecalibacterium prausnitzii* supplementation reduced the area of cardiac fibrosis in mice with myocardial infarction, while the inactivation group did not reduce the cardiac fibrosis area.

Example 3

1. Ultrasound Detection of Mouse Heart

After the breast hairs were depilated and cleaned, the mice were anesthetized with isoflurane, stabilizing the heart rate at 450-500 beats/min. The ultrasound system for small animals (Visual Sonics, Vevo 2100) was used to detect the systolic function of the mouse heart. The B-mode long axis image of the left ventricle of the mouse was collected and the M-mode image was collected at the position having the largest diameter of the left ventricle. Finally, the LV tracking tool was used to calculate the left ventricular ejection fraction and the left ventricular fractional shortening.

2. Hematoxylin and Eosin (HE) Staining and Masson's Trichrome Staining of Mouse Cardiac Muscle Tissue HE staining of mouse cardiac muscle tissue: the paraffin sections were put into the following reagents in chronological order for dewaxing and hydration:

| | |
|---|---|
| Xylene (I) | soaking for 10 min |
| Xylene (II) | soaking for 10 min |
| Xylene (III) | soaking for 10 min |
| Absolute ethanol | soaking for 5 min |
| 95% ethanol | soaking for 5 min |
| 70% ethanol | soaking for 5 min |

The paraffin sections were rinsed with tap water for 15 min. Then the HE staining kit (keygen Cat: KGA 224) was used to stain the sections with the steps as follows:

| | |
|---|---|
| Hematoxylin | staining for 5 min |
| Running water | rinsing for 5 s |
| Eosin | staining for 30 s |
| Running water | rinsing for 5 s |

The sections were air-dried naturally and sealed with a neutral resin and a cover glass. The slides were placed under an upright microscope (NiKon eclipse 80i) for observation, where the cytoplasm of the cardiac tissue was red, the nucleus was purple-blue, the red blood cells were orange-red, and other components were red in different shades. Images were collected by NIS-Elements BR software and the cross-sectional area of cardiac muscle cells was measured with ImageJ. The staining results and statistical results showed that *Faecalibacterium prausnitzii* supplementation reduced the cross-sectional area of cardiac muscle fibers in mice with myocardial infarction, while the inactivation group did not have the effect of reducing the area.

Masson's trichrome staining of mouse cardiac muscle tissue: the paraffin sections were put into the following reagents in chronological order for dewaxing and hydration:

| | |
|---|---|
| Xylene (I) | soaking for 10 min |
| Xylene (II) | soaking for 10 min |
| Xylene (III) | soaking for 10 min |
| Absolute ethanol | soaking for 5 min |
| 95% ethanol | soaking for 5 min |
| 70% ethanol | soaking for 5 min |

The paraffin sections were rinsed with tap water for 15 min. The sections were stained with the Masson's Trichrome Staining Kit (Servicebio, Cat: G1006). Steps were as follows:

| | |
|---|---|
| Potassium dichromate (Masson A solution) | soaking overnight |
| Running water | rinsing for 15 min |
| Hematoxylin (Masson B solution:Masson C solution = 1:1) | staining for 5 min |
| Running water | rinsing for 5 s |
| Ponceau acid fuchsin staining solution (Masson D solution) | staining for 5 min |
| Running water | rinsing for 5 s |
| Phosphomolybdic acid (aqueous solution, Masson E solution) | differentiating for 2 min |
| Aniline blue (Masson F solution) | staining for 1 min |
| Running water | rinsing for 5 s |

The sections were air-dried naturally and sealed with a neutral resin and a cover glass. The slides were placed under an upright microscope (NiKon eclipse 80i) for observation, where the collagen fibers were blue, the cytoplasm of the cardiac muscle tissue was red, and the nucleus was blue-black. Images were collected by NIS-Elements BR software. The area of collagen fibers and the area of cardiac muscle tissue were calculated with ImageJ. Finally, the percentage of collagen fiber area was calculated. The staining results and statistical results showed that *Faecalibacterium prausnitzii* supplementation reduced the area of cardiac fibrosis in mice with myocardial infarction, while the inactivation group did not reduce the cardiac fibrosis area.

3. WGA Staining of Mouse Cardiac Muscle Tissue

The tissue sections produced by frozen sectioning of mouse cardiac muscle tissue were adhered to slides, and the slides were stored at −80° C. A specific staining method was as follows:

| | |
|---|---|
| Rewarming | 15-30 min |
| PBS buffer | washing for 3 times with 5 min a time |
| 4% paraformaldehyde | fixing for 15 min |
| PBS buffer | washing for 3 times with 5 min a time |
| WGA-FITC (sigma#L4895) | incubating for 30 min in the dark |

| | |
|---|---|
| staining solution | |
| PBS buffer | washing for 3 times with 5 min a time |
| Hoechst (keygen#KGA212-1) staining solution | incubating for 30 min in the dark |
| PBS buffer | washing for 3 times with 5 min a time |

After sealing with 50% glycerol in dark, observation was carried out under a fluorescence microscope (Carl Zeiss Microscopy GmbH) (Hoechst excitation wavelength was 375 nm and corresponding emission wavelength was 425 nm, indicated as blue light; WGA-FITC excitation wavelength was 485 nm and emission wavelength was 525 nm, indicated as green light). Images were collected by the ZEN software and the cross-sectional area of cardiac muscle cells was measured with ImageJ. The staining results and statistical results showed that *Faecalibacterium prausnitzii* supplementation reduced the cross-sectional area of cardiac muscle fibers in mice with myocardial infarction, while the inactivation group did not have the effect of reducing the area.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A method for treating pathological ventricular remodeling following myocardial infarction, wherein the method comprises a step of administering a medicine containing *Faecalibacterium prausnitzii* to a patient in need thereof, and the medicine is administered in concentration of viable *Faecalibacterium prausnitzii* bacteria of $10^9$-$10^{12}$ CFU/ml.

2. The method according to claim 1, wherein the *Faecalibacterium prausnitzii* is *Faecalibacterium prausnitzii* VPI C13-51 deposited in American Type Culture Collection (ATCC) with the accession number of ATCC 27768.

3. The method according to claim 2, wherein the *Faecalibacterium prausnitzii* is obtained by culturing the *Faecalibacterium prausnitzii* in a strictly anaerobic environment with a Modified Reinforced Clostridial Culture Medium, wherein the composition of Modified Reinforced Clostridial Culture Medium is listed as below:

| Component | Concentration |
|---|---|
| Tryptose | 10.0 g/L |
| Beef extract | 10.0 g/L |
| Yeast extract | 3.0 g/L |
| Dextrose | 5.0 g/L |
| NaCl | 5.0 g/L |
| Soluble starch | 1.0 g/L |
| L-cysteine HCl | 0.5 g/L |
| Resazurin (0.025%) | 4 ml/L |
| Deionized (DI) water | 1,000 ml |
| Agar | 15 g/L (necessary for solid medium) |
| pH | 6.8. |

4. The method according to claim 2, wherein a dosage form of the medicine is a liquid formulation or a solid formulation.

5. The method according to claim 2, wherein the medicine is an oral formulation.

6. The method according to claim 1, wherein the *Faecalibacterium prausnitzii* is obtained by culturing the *Faecalibacterium prausnitzii* in a strictly anaerobic environment with a Modified Reinforced Clostridial Culture Medium, wherein the composition of Modified Reinforced Clostridial Culture Medium is listed as below:

| Component | Concentration |
|---|---|
| Tryptose | 10.0 g/L |
| Beef extract | 10.0 g/L |
| Yeast extract | 3.0 g/L |
| Dextrose | 5.0 g/L |
| NaCl | 5.0 g/L |
| Soluble starch | 1.0 g/L |
| L-cysteine HCl | 0.5 g/L |
| Resazurin (0.025%) | 4 ml/L |
| Deionized (DI) water | 1,000 ml |
| Agar | 15 g/L (necessary for solid medium) |
| pH | 6.8. |

7. The method according to claim 1, wherein a dosage form of the medicine is a liquid formulation or a solid formulation.

8. The method according to claim 1, wherein the concentration of viable bacteria is $10^{10}$-$10^{11}$ CFU/ml.

9. The method according to claim 1, wherein the medicine is a liquid formulation and is obtained by suspending the *Faecalibacterium prausnitzii* in a phosphate buffer.

10. The method according to claim 9, wherein the phosphate buffer further comprises glycerol in a volume percentage of 10%.

11. The method according to claim 1, wherein the medicine is an oral formulation.

* * * * *